United States Patent [19]

Irvine et al.

[11] Patent Number: 5,736,316
[45] Date of Patent: Apr. 7, 1998

[54] HBV CAPTURE AND AMPLIFIERS PROBES FOR USE IN SOLUTION PHASE SANDWICH HYBRIDIZATION ASSAYS

[75] Inventors: Bruce D. Irvine, Concord; Janice A. Kolberg, Hercules; Joyce A. Running, Concord; Michael S. Urdea, Alamo, all of Calif.

[73] Assignee: Chiron Corporation, Emeryville, Calif.

[21] Appl. No.: 186,229

[22] Filed: Jan. 24, 1994

Related U.S. Application Data

[63] Continuation of Ser. No. 813,586, Dec. 23, 1991, abandoned.

[51] Int. Cl.$^6$ .............. C12Q 1/70; C12Q 1/68; C07H 21/02
[52] U.S. Cl. .................. 435/5; 435/6; 536/23.1
[58] Field of Search ................ 435/6; 536/23.1, 536/24.32

[56] References Cited

U.S. PATENT DOCUMENTS

| | | | |
|---|---|---|---|
| 4,562,159 | 12/1985 | Shafritz et al. | 436/50 |
| 4,868,105 | 9/1989 | Urdea et al. | 435/6 |
| 5,008,182 | 4/1991 | Sninsky et al. | 435/5 |
| 5,124,246 | 6/1992 | Urdea et al. | 435/6 |

FOREIGN PATENT DOCUMENTS

| | | | |
|---|---|---|---|
| 068719 | 6/1982 | European Pat. Off. | |
| 0278940 | 8/1988 | European Pat. Off. | |
| 0317077 | 5/1989 | European Pat. Off. | C12Q 1/68 |
| 2034323 | 6/1980 | United Kingdom | |
| WO89/03891 | 5/1989 | WIPO | C12Q 1/68 |
| 9013667 | 11/1990 | WIPO | C12Q 1/68 |

OTHER PUBLICATIONS

Kobayashi et al., "Complete nucleotide sequence of hepatitis B virus DNA of subtype adr and its conserved gene organization" *Gene* (1984) 30:227–232.

Pasek et al., *Nature* (1979) 282:575–579.

Valenzuela et al., *Animal Virus Genetics* (1981) Field et al., Eds., Academic Press, New York, pp. 57–70.

Fujiyama et al., *Nucleic Acids Research* (1983) 11:4601–4610.

Berninger et al., *J. Med. Virol.* (1982) 9:57–68.

U.S. Patent Application Serial Number 07/558,897 (filed 27 Jul. 1990).

Sherlock et al., *J. Amer. Med. Assoc.* (1984) 252(3):402–406.

Ono, Y., et al. The Complete Nucleotide Sequences of the Cloned Hepatitis B Virus DNA: Subtype ADR and ADW. Nucl. Acids Res. (1983) 11: 1747–1757.

Blum, H.E, et al. Asymmetric Replication of Hepatitis B Virus DNA In Human Liver Demonstration of Cytoplasmic . . . Virology (1984) 139:87–96.

Stratagene Catalog, 1988, p. 39.

*Primary Examiner*—Eggerton A. Campbell
*Attorney, Agent, or Firm*—Tyler Dylan; Kenneth M. Goldman; Robert P. Blackburn

[57] ABSTRACT

Novel DNA probe sequences for detection of HBV in a sample in a solution phase sandwich hybridization assay are described. Amplified nucleic acid hybridization assays using the probes are exemplified.

14 Claims, No Drawings

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGACTGR        7

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGTGGAGACA CGGGTCCTAT GCCT        24

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GATGTGGTTG  TCGTACTTGA  TGTGGTTGTC  GTACTTGATG  TGGTTGTCGT  ACTTGCGTAG         60
```

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TCCACGAAAA  AAAAAA                                                             16
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CAGTCACTAC  GC                                                                 12
```

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
TTGTGGGTCT  TTTGGG Y TTT  GCTGC Y CCWT                                         30
```

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
CCTKCTCGTG  TTACAGGCGG  GGTTTTCTT                                              30
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
TCCATGGCTG  CTAGGSTGTR  CTGCCAACTG                                             30
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GCYTAYAGAC  CACCAAATGC  CCCTAT-                                  30
CYTA
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
CTGTTCAAGC  CTCCAAGCTG  TGCCTTGGGT                               30
```

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CATGGAGARC  AYMACATCAG  GATTCCTAGG                               30
```

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TCCTGGYTAT  CGCTGGATGT  GTCTGCGGCG  T                            31
```

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GGCGCTGAAT  CCYGCGGACG  ACCCBTCTCG                               30
```

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
CTTCGCTTCA  CCTCTGCACG  THGCATGGMG                               30
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
GGTCTSTGCC  AAGTGTTTGC  TGACGCAACC                               30
```

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCTKCGCGGG ACGTCCTTTG T Y TACGTCCC        30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

MCCTCTGCCT AATCATCTCW TGTWCATGTC        30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CGACCACGGG GCGCACCTCT CTTTACGCGG        30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TGCCCAAGGT CTTACA Y AAG AGGACTCTTG        30

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CGTCAATCT Y CKCGAGGACT GGGGACCCTG        30

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

ATGTTGCCCG TTTGTCCTCT AMTTCCAGGA        30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ATCTTCTTRT TGGTTCTTCT GGA Y TA Y CAA         30

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ATCATMTTCC TCTTCATCCT GCTGCTATGC         30

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CAATCACTCA CCAACCTC Y T GTCCTCCAA Y         30

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GTGTC Y TGGC CAAAATTCGC AGTCCCCAAC         30

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CTCGTGGTGG ACTTCTCTCA ATTTTCTAGG         30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GACAAGAATC CTCACAATAC CRCAGAGTCT         30

( 2 ) INFORMATION FOR SEQ ID NO:28:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

TTTTGGGGTG GAGCCCKCAG GCTCAGGGCR　　　　　　　　　　　　　　　　　30

( 2 ) INFORMATION FOR SEQ ID NO:29:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

CACCATATTC TTGGGAACAA GAKCTACAGC　　　　　　　　　　　　　　　　　30

( 2 ) INFORMATION FOR SEQ ID NO:30:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

ACACTTCCGG ARACTACTGT TGTTAGACGA　　　　　　　　　　　　　　　　　30

( 2 ) INFORMATION FOR SEQ ID NO:31:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

GTVTCTTT Y G GAGTGTGGAT TCGCACTCCT　　　　　　　　　　　　　　　　　30

( 2 ) INFORMATION FOR SEQ ID NO:32:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

TTGGAGCWWC TGTGGAGTTA CTCTCKTTTT　　　　　　　　　　　　　　　　　30

( 2 ) INFORMATION FOR SEQ ID NO:33:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

TTTGGGGCAT GGACAT Y GA Y CCKTATAAAG　　　　　　　　　　　　　　　　30

( 2 ) INFORMATION FOR SEQ ID NO:34:

( i ) SEQUENCE CHARACTERISTICS:
    ( A ) LENGTH: 30 base pairs (B) TYPE: nucleic acid
(C) STRANDEDNESS: single
(D) TOPOLOGY: linear (xi) SEQUENCE DESCRIPTION: SEQ ID NO:34:

AAWGRTCTTT GTAYTAGGAG GCTGTAGGCA　　　　　　　　　　　　　　　　30

(2) INFORMATION FOR SEQ ID NO:35:

(i) SEQUENCE CHARACTERISTICS:
　　(A) LENGTH: 30 base pairs
　　(B) TYPE: nucleic acid
　　(C) STRANDEDNESS: single
　　(D) TOPOLOGY: linear (xi) SEQUENCE DESCRIPTION: SEQ ID NO:35:

RGACTGGGAG GAGYTGGGGG AGGAGATTAG　　　　　　　　　　　　　　　　30

(2) INFORMATION FOR SEQ ID NO:36:

(i) SEQUENCE CHARACTERISTICS:
　　(A) LENGTH: 30 base pairs
　　(B) TYPE: nucleic acid
　　(C) STRANDEDNESS: single
　　(D) TOPOLOGY: linear (xi) SEQUENCE DESCRIPTION: SEQ ID NO:36:

CCTTGAGGCM TACTTCAAAG ACTGTKTGTT　　　　　　　　　　　　　　　　30

(2) INFORMATION FOR SEQ ID NO:37:

(i) SEQUENCE CHARACTERISTICS:
　　(A) LENGTH: 30 base pairs
　　(B) TYPE: nucleic acid
　　(C) STRANDEDNESS: single
　　(D) TOPOLOGY: linear (xi) SEQUENCE DESCRIPTION: SEQ ID NO:37:

GTCTGTGCCT TCTCATCTGC CGGWCCGTGT　　　　　　　　　　　　　　　　30

(2) INFORMATION FOR SEQ ID NO:38:

(i) SEQUENCE CHARACTERISTICS:
　　(A) LENGTH: 30 base pairs
　　(B) TYPE: nucleic acid
　　(C) STRANDEDNESS: single
　　(D) TOPOLOGY: linear (xi) SEQUENCE DESCRIPTION: SEQ ID NO:38:

AGCMGCTTGT TTTGCTCGCA GSMGGTCTGG　　　　　　　　　　　　　　　　30

(2) INFORMATION FOR SEQ ID NO:39:

(i) SEQUENCE CHARACTERISTICS:
　　(A) LENGTH: 30 base pairs
　　(B) TYPE: nucleic acid
　　(C) STRANDEDNESS: single
　　(D) TOPOLOGY: linear (xi) SEQUENCE DESCRIPTION: SEQ ID NO:39:

GGCTCSTCTG CCGATCCATA CTGCGGAACT　　　　　　　　　　　　　　　　30

(2) INFORMATION FOR SEQ ID NO:40:

(i) SEQUENCE CHARACTERISTICS:
　　(A) LENGTH: 30 base pairs
　　(B) TYPE: nucleic acid
　　(C) STRANDEDNESS: single ( D ) TOPOLOGY: linear ( x i ) SEQUENCE DESCRIPTION: SEQ ID NO:40:

MTKAACCTTT ACCCCGTTGC TCGGCAACGG  30

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GTGGCTCCAG TTCMGGAACA GTAAACCCTG  30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

KAARCAGGCT TT Y ACTTTCT CGCCAACTTA  30

( 2 ) INFORMATION FOR SEQ ID NO:43:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CCTCCKCCTG CCTC Y ACCAA TCGSCAGTCA  30

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

ACCAATTTTC TT Y TGTCT Y T GGGTATACAT  30

( 2 ) INFORMATION FOR SEQ ID NO:45:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

TATTCCCATC CCATCRTCCT GGGCTTTCGS  30

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

TATATGGATG ATGTGGTATT GGGGGCCAAG 30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

CGTAGGGCTT TCCCCCACTG TTTGGCTTTC 30

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GCTCAGTTTA CTAGTGCCAT TTGTTCAGTG 30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CCTATGGGAG KGGGCCTCAG YCCGTTCTC 30

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GTCCCCTAGA AGAAGAACTC CCTCGCCTCG 30

( 2 ) INFORMATION FOR SEQ ID NO:51:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

ACGMAGRTCT CMATCGCCGC GTCGCAGAAG A 31

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

-continued

```
CAATCTCGGG AATCTCAATG TTAGTATYCC                                    30
```

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

```
GACTCATAAG GTSGGRAACT TTACKGGGCT                                    30
```

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

```
AGGCATAGGA CCCGTGTCTT                                               20
```

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
CTTCTTTGGA GAAAGTGGTG                                               20
```

HBV CAPTURE AND AMPLIFIERS PROBES FOR USE IN SOLUTION PHASE SANDWICH HYBRIDIZATION ASSAYS

This application is a continuation of application Ser. No. 07/813,586, filed Dec. 23, 1991, now abandoned.

TECHNICAL FIELD

This invention is in the field of nucleic acid hybridization assays. More specifically, it relates to novel nucleic acid probes for detecting Hepatitis B Virus (HBV).

BACKGROUND ART

Viral hepatitis is a systemic disease involving primarily the liver, with HBV being primarily responsible for most cases of serum or long-incubation hepatitis.

Antigenic characterization of HBV derives from the complex protein found on the virus's surface. One antigenic specificity, designated a, is common to all HBV surface antigen (HBsAg), while two other sets of mutually exclusive determinants result in four principle subtypes of HBsAg: adw, ayw, adr, and ayr.

Paset et al. (*Nature* 282:575–579, 1979) disclosed the entire nucleotide sequence of subtype ayw HBV genomic DNA.

Valenzuela et al. (*Animal Virus Genetics*, Field et al., eds., Academic press, NY, 1981) reported the complete nucleotide sequence of subtype adw2 HBV DNA.

EPA Pub. No. 0068719 disclosed the sequence and expression of HBsAg from the adw serotype.

Fujiyama et al. (*Nucleic Acid Research* 11:4601–4610, 1983) disclosed the entire nucleotide sequence of serotype adr HBV DNA.

British patent application No. 2034323A, published Jun. 4, 1980, describes the isolation and cloning of the HBV genome and its use to detect HBV in serum.

Berninger et al. (*J. Med. Virol.* 9:57–68, 1982) discloses an assay based on nucleic acid hybridization which detects and quantitates HBV in serum, using the complete HBV genome as probe.

U.S. Pat. No. 4,562,159, issued 31 Dec. 1985 discloses a method and test kit for the detection of HBV by DNA hybridization using cloned, genomic HBV DNA as a probe.

Commonly owned U.S. Pat. No. 4,868,105, issued 19 Sep. 1989 describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is substantially complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned European Patent Application (EPA) 883096976 published as E.P.O. Pub. No. 0317077 discloses a variation in the assay described in U.S. Pat. No. 4,868,105, issued 19 Sep. 1989, in which the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified. Amplifier and capture probe sequences are disclosed for Hepatitis B virus, *Neisseria gonorrhoeae*, penicillin and tetracycline resistance in *N. gonorrhoeae*, and *Chlamydia trachomatis*.

Commonly owned copending application Ser. No. 558,897, filed 27 Jul. 1990, describes the preparation of large comb-type branched polynucleotide multimers for use in the above-described solution phase assay. The combs provide greater signal enhancement in the assays than the smaller multimers.

DISCLOSURE OF THE INVENTION

One aspect of the invention is a synthetic oligonucleotide useful as an amplifier probe in a sandwich hybridization assay for HBV comprising a first segment having a nucleotide sequence substantially complementary to a segment of HBV nucleic acid and a second segment having a nucleotide sequence substantially complementary to an oligonucleotide multimer.

Another aspect of the invention is a synthetic oligonucleotide useful as a capture probe in a sandwich hybridization assay for HBV comprising a first segment having a nucleotide sequence substantially complementary to a segment of HBV nucleic acid and a second segment having a nucleotide sequence substantially complementary to an oligonucleotide bound to a solid phase.

Another aspect of the invention is a solution sandwich hybridization assay for detecting the presence of HBV in a sample, comprising (a) contacting the sample under hybridizing conditions with an excess of (i) an amplifier probe oligonucleotide comprising a first segment having a nucleotide sequence substantially complementary to a segment of HBV nucleic acid and a second segment having a nucleotide sequence substantially complementary to an oligonucleotide unit of a nucleic acid multimer and (ii) a capture probe oligonucleotide comprising a first segment having a nucleotide sequence that is substantially complementary to a segment of HBV nucleic acid and a second segment that is substantially complementary to an oligonucleotide bound to a solid phase;

(b) contacting the product of step (a) under hybridizing conditions with said oligonucleotide bound to the solid phase;

(c) thereafter separating materials not bound to the solid phase;

(d) contacting the bound product of step (c) under hybridization conditions with the nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Another aspect of the invention is a kit for the detection of HBV comprising a kit for the detection of HBV in a sample comprising in combination (i) a set of amplifier probe oligonucleotides wherein the amplifier probe oligonucleotide comprises a first segment having a nucleotide sequence substantially complementary to a segment of HBV nucleic acid and a second segment having a nucleotide sequence substantially complementary to an oligonucleotide unit of a nucleic acid multimer;

(ii) a set of capture probe oligonucleotides wherein the capture probe oligonucleotide comprises a first segment having a nucleotide sequence that is substantially complementary to a segment of HBV nucleic acid and a second segment that is substantially complementary to an oligonucleotide bound to a solid phase;

(iii) a nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide; and (iv) a labeled oligonucleotide.

These and other embodiments will readily occur to those of ordinary skill in view of the disclosure herein.
Modes for Carrying out the Invention Definitions In defining the present invention, the following terms will be employed, and are intended to be defined as indicated below.

"Solution phase nucleic acid hybridization assay" intends the assay techniques described and claimed in commonly owned U.S. Pat. No. 4,868,105 and EPA 883096976.

A "modified nucleotide" intends a nucleotide monomer that may be stably incorporated into a polynucleotide and which has an additional functional group. Preferably, the modified nucleotide is a 5'-cytidine in which the $N^4$-position is modified to provide a functional hydroxy group.

An "amplifier multimer" intends a branched polynucleotide that is capable of hybridizing simultaneously directly or indirectly to analyte nucleic acid and to a multiplicity of polynucleotide iterations (i.e., either iterations of another multimer or iterations of a labeled probe). The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EPA 883096976 published as E.P.O Pub. No. 0317077 and U.S. Ser. No. 558,897 filed 27 Jul. 1990, the disclosures of which are incorporated herein by reference.

The term "amplifier probe" is intended as a branched or linear polynucleotide that is constructed to have a segment that hybridizes specifically to the analyte nucleic acid and iterations of a second segment that hybridize specifically to an amplifier multimer.

The term "capture probe" is intended as an oligonucleotide having a segment substantially complementary to a nucleotide sequence of the target DNA and a segment that is substantially complementary to a nucleotide sequence of a solid-phase-immobilized probe.

"Large" as used herein to describe the comb-type branched polynucleotides of the invention intends a molecule having at least about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "cleavable linker molecule" intends a molecule that may be stably incorporated into a polynucleotide chain and which includes a covalent bond that may be broken or cleaved by chemical treatment or physical treatment such as by irradiation.

All nucleic acid sequences disclosed herein are written in a 5' to 3' direction unless otherwise indicated. Nucleotides are designated according to the nucleotide symbols recommended by the IUPAC-IUB Biochemical Nomenclature.
Solution Phase Hybridization Assay The general protocol for the solution phase sandwich hybridizations is as follows. The analyte nucleic acid is placed in a microtiter well with an excess of two single-stranded nucleic acid probe sets: (1) a set of capture probes, each having a first binding sequence substantially complementary to the analyte and a second binding sequence that is substantially complementary to nucleic acid bound to a solid support, for example, the well surface or a bead, and (2) a set of amplifier probes (branched or linear), each having a first binding sequence that is capable of specific binding to the analyte and a second binding sequence that is capable of specific binding to a segment of the multimer. The resulting product is a three component nucleic acid complex of the two probes hybridized to the analyte by their first binding sequences. The second binding sequences of the probes remain as single-stranded segments as they are not complementary to the analyte. This complex hybridizes to the immobilized probe on the solid surface via the second binding sequence of the capture probe. The resulting product comprises the complex bound to the solid surface via the duplex formed by the oligonucleotide bound to the solid surface and the second binding sequence of the capture probe. Unbound materials are then removed from the surface such as by washing.

The amplification multimer is then added to the bound complex under hybridization conditions to permit the multimer to hybridize to the available second binding sequence (s) of the amplifier probe of the complex. The resulting complex is then separated from any unbound multimer by washing. The labeled oligonucleotide is then added under conditions which permit it to hybridize to the substantially complementary oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, and may be prepared for the hybridization analysis by a variety of means, e.g., proteinase K/SDS, chaotropic salts, etc. Also it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2M hydroxide, formamide, salts, heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The number of different amplifier and capture probes used influences the sensitivity of the assay, because the more probe sequences used, the greater the signal provided by the assay system. Furthermore, the use of more probe sequences allows the use of more stringent hybridization conditions, thereby reducing the incidence of false positive results. Thus, the number of probes in a set will be at least one capture probe and at least one amplifier probe, more preferably two capture and two amplifier probes and most preferably 5-100 capture probes and 5-100 amplifier probes.

Probes for HBV were designed as follows. EPA 88309676 published as E.P.O. Pub. No. 0317077 discloses a set of HBV probes designed by comparing the DNA sequences of the nine HBV subtypes reported in GenBank. Subsequent experimental analysis has demonstrated that these probes were complementary to the subgenomic strand (i.e, plus sense) of the incompletely double-stranded region of HBV, and thus different subsets of these probes hybridized to different viruses, since the length of the subgenomic strands varies among strains. Accordingly, the probe set has been redesigned to comprise sequences substantially complementary to the genomic-length strand (i.e, minus-sense) of HBV and to contain fewer spacer regions so as to include more oligonucleotides in the probe set, thereby increasing the sensitivity of the assay system.

In general, regions of greatest homology between the HBV isolates were selected as capture probes, while regions of lesser homology were selected as amplifier probes. Thus, as additional strains or isolates of HBV are made available, appropriate probes may be designed by aligning the sequence of the new strain or isolate with the nucleotide sequences used to design the probes of the present invention, and choosing regions of greatest homology for use as capture probes, with regions of lesser homology chosen as amplifier probes. The set of presently preferred probes and their capture or amplifier overhang regions, i.e., the regions which hybridize to sequences immobilized on solid support or to an amplifier multimer, are listed in the examples.

The second binding sequences of the capture probe and amplifier probe are selected to be substantially complementary, respectively, to the oligonucleotide bound to the solid surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

The labeled oligonucleotide will include a sequence substantially complementary to the repeated oligonucleotide units of the multimer. The labeled oligonucleotide will include one or more molecules ("labels"), which directly or indirectly provide a detectable signal. The labels may be bound to individual members of the substantially complementary sequence or may be present as a terminal member or terminal tail having a plurality of labels. Various means for providing labels bound to the oligonucleotide sequences have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids. Res.* (1985) 13:2399; Meinkoth and Wahl, *Anal. Biochem.* (1984) 138:267. The labels may be bound either covalently or non-covalently to the substantially complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, α-β-galactosidase, horse-radish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to $10^{6:1}$. Concentrations of each of the probes will generally range from about $10^{-5}$ to $10^{-9}$M, with sample nucleic acid concentrations varying from $10^{-21}$ to $10^{-12}$M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reactions are usually done in an aqueous medium, particularly a buffered aqueous medium, which may include various additives. Additives which may be employed include low concentrations of detergent (0.01 to 1%), salts, e.g., sodium citrate (0.017 to 0.17M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

Kits for carrying out amplified nucleic acid hybridization assays according to the invention will comprise in packaged combination the following reagents: the amplifier probe or set of probes; the capture probe or set of probes; the amplifier multimer; and an appropriate labeled oligonucleotide. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples further illustrate the invention. These examples are not intended to limit the invention in any manner.

EXAMPLES

Example I

Synthesis of Comb-type Branched Polynucleotide

This example illustrates the synthesis of a comb-type branched polynucleotide having 15 branch sites and sidechain extensions having three labeled probe binding sites. This polynucleotide was designed to be used in a solution phase hybridization as described in EPA 883096976.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed PHOSTEL™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl)(ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

3'T$_{15}$(TTX')$_{15}$GTTTGTGG-5'
|
(RGTCAGTp-5')$_{15}$ wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

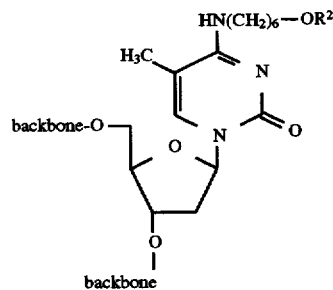

where R$^2$ represents

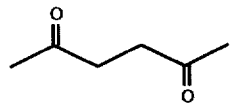

For synthesis of the comb body (not including sidechains), the concentration of beta cyanoethylphosphoramidite monomers was 0.1M for A, C, G and T, 0.15M for the branching site monomer E, and 0.2M for PHOSTEL™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl). Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal (R$^2$ in the formula above) was performed manually while retaining the CPG support in the same column used for synthesizing the comb body. In the case of R$^2$=levulinyl, a solution of 0.5M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1M (except 0.2M R and PHOSTEL™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl); R was 2-(4-(4-(2-Dimethoxytrityloxy)ethyl-)phenoxy 2,3-di(benzoyloxy)-butyloxy) phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH$_3$." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 µl water.

3' backbone extensions (segment A), sidechain extensions and ligation template/linkers of the following structures were also made using the automatic synthesizer:

| | | |
|---|---|---|
| 3' Backbone extension | 3'-TCCGTATCCTGGGCACAGAGGTGCp-5' | (SEQ ID NO: 2) |
| Sidechain extension | 3'-GATGCG(TTCATGCTGTTGGTGTAG)₃-5' | (SEQ ID NO: 3) |
| Ligation template for linking 3' backbone extension | 3'-AAAAAAAAAAGCACCTp-5' | (SEQ ID NO: 4) |
| Ligation template for linking sidechain extension | 3'-CGCATCACTGAC-5' | (SEQ ID NO: 5) |

The crude comb body was purified by a standard polyacrylamide gel (7% with 7M urea and 1X TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl), sidechain linking template (75 pmoles/μl) and backbone linking template (5 pmole/μl) were combined in 1 mM ATP/ 5 mM DTT/50 mM Tris-HCl, pH 8.0/10 mM MgC₂/ 2 mM spermidine, with 0.5 units/μl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/μl T4 ligase were added, and the mixture incubated for 16–24 hr at 23° C. The DNA was precipitated in NaCl/ethanol, resuspended in water, and subjected to a second ligation as follows. The mixture was adjusted to 1 mM ATP, 5 mM DTT, 14% polyethylene glycol, 50 mM Tris-HCl, pH 7.5, 10 mM MgCl₂, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

After ligation and purification, a portion of the product was labeled with $^{32}$p and subjected to cleavage at the site of R achieved by oxidation with aqueous NaIO₄ for 1 hr. The sample was then analyzed by PAGE to determine the number of sidechain extensions incorporated by quantitating the radioactive label in the bands on the gel. The product was found to have a total of 45 labeled probe binding sites.

Example 2

Hybridization Assay for HBV DNA

A "15×3" amplified solution phase nucleic acid sandwich hybridization assay format was employed in this example. The "15×3" designation derives from the fact that the format employs two multimers: (1) an amplifier probe having a first segment (A) that binds to HBV nucleic acid and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe segments and their respective names used in this assay were as follows.

HBV AMPLIFIER PROBES

HBV.104* (SEQ ID NO:6) TTGTGGGTCTTTTGGGYTTTGCTGCYCCWT

HBV.94* (SEQ ID NO:7) CCTKCTCGTGTTACAGGCGGGGTTTTTCTT

HBV.76* (SEQ ID NO:8) TCCATGGCTGCTAGGSTGTRCTGCCAACTG

HBV.87* (SEQ ID NO:9) GCYTAYAGACCACCAAATGCCCCTATCYTA

HBV.45* (SEQ ID NO:10) CTGTTCAAGCCTCCAAGCTGTGCCTTGGGT

HBV.93* (SEQ ID NO:11) CATGGAGARCAYMACATCAGGATTCCTAGG

HBV.99* (SEQ ID NO:12) TCCTGGYTATCGCTGGATGTGTCTGCGGCGT

HBV.78* (SEQ ID NO:13) GGCGCTGAATCCYGCGGACGACCCBTCTCG

HBV.81* (SEQ ID NO:14) CTTCGCTTCACCTCTGCACGTHGCATGGMG

HBV.73*070590-C (SEQ ID NO:15) GGTCTSTGCCAAGTGTTTGCTGACGCAACC

HBV.77*070590-b (SEQ ID NO:16) CCTKCGCGGGACGTCCTTTGTYTACGTCCC

HBV.D44*070590-A (SEQ ID NO:17) MCCTCTGCCTAATCATCTCWTGTWCATGTC

HBV.79* (SEQ ID NO:18) CGACCACGGGGCGCACCTCTCTTTACGCGG

HBV.82* (SEQ ID NO:19) TGCCCAAGGTCTTACAYAAGAGGACTCTTG

HBV.71* (SEQ ID N0:20) CGTCAATCTYCKCGAGGACTGGGGACCCTG

HBV.102* (SEQ ID NO:21) ATGTTGCCCGTTTGTCCTCTAMTTCCAGGA

HBV.101* (SEQ ID N0:22) ATCTTCTTRTTGGTTCTTCTGGAYTAYCAA

HBV.100* (SEQ ID NO:23) ATCATMTTCCTCTTCATCCTGCTGCTATGC

HBV.98* (SEQ ID N0:24) CAATCACTCACCAACCTCYTGTCCTCCAAY

HBV.97* (SEQ ID NO:25) GTGTCYTGGCCAAAATTCGCAGTCCCCAAC

HBV.96* (SEQ ID N0:26) CTCGTGGTGGACTTCTCTCAATTTTCTAGG

HBV.95* (SEQ ID NO:27) GACAAGAATCCTCACAATACCRCAGAGTCT

HBV.92* (SEQ ID N0:28) TTTTGGGGTGGAGCCCKCAGGCTCAGGGCR

HBV.91* (SEQ ID NO:29) CACCATATTCTTGGGAACAAGAKCTACAGC

HBV.88* (SEQ ID NO:30) ACACTTCCGGARACTACTGTTGTTAGACGA

HBV.86* (SEQ ID NO:31) GTVTCTTTYGGAGTGTGGATTCGCACTCCT

HBV.D47* (SEQ ID N0:32) TTGGAGCWWCTGTGGAGTTACTCTCKTTTT

HBV.D46* (SEQ ID N0:33) TTTGGGGCATGGACATYGAYCCKTATAAAG

HBV.85* (SEQ ID N0:34) AAWGRTCTTTGTAYTAGGAGGCTGTAGGCA

HBV.84* (SEQ ID NO:35) RGACTGGGAGGAGYTGGGGGAGGAGATTAG

HBV.83* (SEQ ID N0:36) CCTTGAGGCMTACTTCAAAGACTGTKTGTT

HBV.80* (SEQ ID N0:37) GTCTGTGCCTTCTCATCT-
GCCGGWCCGTGT
HBV.75* (SEQ ID NO:38) AGCMGCTTGTTTTGCTCG-
CAGSMGGTCTGG
HBV.74* (SEQ ID NO:39) GGCTCSTCTGCCGATCCAT-
ACTGCGGAACT
HBV.72* (SEQ ID NO:40) MTKAACCTTTACCCCGT-
TGCTCGGCAACGG
HBV.51* (SEQ ID NO:41) GTGGCTCCAGTTCMGGAA-
CAGTAAACCCTG
HBV.67* (SEQ ID N0:42) KAARCAGGCTTTY-
ACTTTCTCGCCAACTTA
HBV.70* 062890-A (SEQ ID NO:43) CCTCCKCCTGCCT-
CYACCAATCGSCAGTCA
HBV.65* (SEQ ID NO:44) ACCAATTTTCTTYTGTC-
TYTGGGTATACAT

HBV Capture Probes

HBV.60* (SEQ ID NO:45) TATTCCCATCCCATCrTC-
CTGGGCTTTCGS
HBV.64* (SEQ ID NO:46) TATATGGATGATGTGGTAT-
TGGGGGCCAAG
HBV.63* (SEQ ID NO:47) CGTAGGGCTTTCCCCCACT-
GTTTGGCTTTC
HBV.62* (SEQ ID N0:48) GCTCAGTTTACTAGTGC-
CATTTGTTCAGTG
HBV.61* (SEQ ID N0:49)
CCTATGGGAGKGGGCCTCAGYCCGTTTCTC
HBV.89* (SEQ ID NO:50)
GTCCCCTAGAAGAAGAACTCCCTCGCCTCG
HBV.90* (SEQ ID NO:51)
ACGMAGRTCTCMATCGCCGCGTCGCAGAAGA
HBV.D13* (SEQ ID NO:52)
CAATCTCGGGAATCTCAATGTTAGTATYCC
HBV.D14* (SEQ ID NO:53) GACTCATAAGGTSG-
GRAACTTTACKGGGCT

Each amplifier probe contained, in addition to the sequences substantially complementary to the HBV sequences, the following 5' extension complementary to a segment of the amplifier multimer,
AGGCATAGGACCCGTGTCTT (SEQ ID NO:54).

Each capture probe contained, in addition to the sequences substantially complementary to HBV DNA, the following downstream sequence complementary to DNA bound to the solid phase (i.e, complementary to XT1*),
CTTCTTTGGAGAAAGTGGTG (SEQ ID NO:55).

Microtiter plates were prepared as follows. White Microlite 1 Removawell strips (polystyrene microtiter plates, 96 wells/plate) were purchased from Dynatech Inc. Each well was filled with 200 µl 1 N HCl and incubated at room temperature for 15–20 min. The plates were then washed 4 times with 1X PBS and the wells aspirated to remove liquid. The wells were then filled with 200 µl 1 N NaOH and incubated at room temperature for 15–20 min. The plates were again washed 4 times with 1X PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1X PBS to a final concentration of 0.1 mg/ml (pH 6.0). 100 µl of this solution was added to each well. The plate was wrapped in plastic to prevent drying and incubated at 30° C. overnight. The plate was then washed 4 times with 1X PBS and the wells aspirated to remove liquid.

The following procedure was used to couple the oligonucleotide XT1* to the plates. Synthesis of XT1* was described in EPA 883096976. 20 mg disuccinimidyl suberate was dissolved in 300 µl dimethyl formamide (DMF). 26 $OD_{260}$ units of XT1* was added to 100 µl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated XT1* DNA was eluted from the column with 3.5 ml 10 mM sodium phosphate, pH 6.5. 5.6 $OD_{260}$ units of eluted DSS-activated XT1* DNA was added to 1500 ml 50 mM sodium phosphate, pH 7.8. 50 µl of this solution was added to each well and the plates were incubated overnight. The plate was then washed 4 times with 1X PBS and the wells aspirated to remove liquid.

Final stripping of plates was accomplished as follows. 200 µL of 0.2N NaOH containing 0.5% (w/v) SDS was added to each well. The plate was wrapped in plastic and incubated at 65° C. for 60 min. The plate was then washed 4 times with 1X PBS and the wells aspirated to remove liquid. The stripped plate was stored with desiccant beads at 2°–8° C.

Sample preparation consisted of delivering 12.5 µl P-K buffer (2 mg/ml proteinase K in 10 mM Tris-HCl, pH 8.0/0.15M NaCl/10 mM EDTA, pH 8.0/1% SDS/40 µg/ml sonicated salmon sperm DNA) to each well. A standard curve of HBV DNA was prepared by diluting cloned HBV, subtype adw, DNA in HBV negative human serum and delivering aliquots of dilutions corresponding to 1000, 3000, 10,000, 30,000, or 100,000 molecules to each well. Tests for cross-hybridization to heterologous DNAs were done by adding either purified DNA or infected cells to each well. Amounts for each organism are indicated in the Table.

Plates were covered and agitated to mix samples, then incubated at 65° C. to release nucleic acids.

A cocktail of the HBV-specific amplifier and capture probes listed above was added to each well (5 fmoles of each probe/well, diluted in 1 N NaOH). Plates were covered and gently agitated to mix reagents and then incubated at 65° C. for 30 min.

Neutralization buffer was then added to each well (0.77M 3-(N-morpholino)propane sulfonic acid/1.845 M NACl/ 0.185 sodium citrate). Plates were covered and incubated for 12–18 hr at 65° C.

After an additional 10 min at room temperature, the contents of each well were aspirated to remove all fluid, and the wells washed 2X with washing buffer (0.1% SDS/ 0.015M NaCl/0.0015 sodium citrate).

Amplifier multimer was then added to each well (30 fmoles/well). After covering plates and agitating to mix the contents in the wells, the plates were incubated for 30 min at 55° C.

After a further 5–10 min period at room temperature, the wells were washed as described above.

Alkaline phosphatase label probe, disclosed in EP 883096976, was then added to each well (40 µl/well of 2.5 fmoles/µl). After incubation at 55° C. for 15 min, and 5 min at room temperature, the wells were washed twice as above and then 3X with 0.015M NACl/0.0015M sodium citrate.

An enzyme-triggered dioxetane (Schaap et al., Tet. Lett. (1987) 28:1159–1162 and EPA Pub. No. 0254051), obtained from Lumigen, Inc., was employed. 20 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results from an exclusivity study of the HBV probes is shown in the Table below. Results for each standard sample are expressed as the difference between the mean of the negative control plus two standard deviations and the mean of the sample minus two standard deviations (delta). If delta is greater than zero, the sample is considered positive. These results indicate the ability of these probe sets to distinguish HBV DNA from heterologous organisms and a sensitivity of about 1000–3000 HBV molecules.

TABLE

| Sample | Amount | Delta |
| --- | --- | --- |
| HBV | $1 \times 10^5$ | 25.99 |
| HBV | $3 \times 10^4$ | 6.51 |
| HBV | $1 \times 10^4$ | 3.00 |
| HBV | $3 \times 10^3$ | 0.93 |
| HBV | $1 \times 10^3$ | −0.20 |
| Control | — | — |
| HCV | $8 \times 10^5$ | −0.39 |
| CMV[1] | $3.3 \times 10^6$ | −0.48 |
| HTLV-II[2] | $1 \times 10^5$ | −0.07 |
| HTLV-I[2] | $1 \times 10^5$ | −0.23 |
| HIV | $1 \times 10^7$ | −0.31 |
| pBR325 | $1 \times 10^7$ | −0.27 |
| Streptococcus sanguis | $1 \times 10^7$ | −0.31 |
| Streptococcus pyogenes | $1 \times 10^7$ | −0.36 |

TABLE-continued

| Sample | Amount | Delta |
| --- | --- | --- |
| Streptococcus pneumoniae | $1 \times 10^7$ | −0.38 |
| Streptococcus fecalis | $1 \times 10^7$ | −0.28 |
| Streptococcus agalactiae | $1 \times 10^7$ | −0.26 |
| Streptococcus epidermidis | $1 \times 10^7$ | −0.31 |
| Staphylococcus aureus | $1 \times 10^7$ | −0.34 |
| Serratia marcescens | $1 \times 10^7$ | −0.30 |
| Pseudomonas aeruginosa | $1 \times 10^7$ | −0.23 |
| Proteus mirabilis | $1 \times 10^7$ | −0.43 |
| Peptostreptococcus anerobius | $1 \times 10^7$ | −0.46 |
| Lactobacillus acidophilus | $1 \times 10^7$ | −0.33 |
| Klebsiella pneumoniae | $1 \times 10^7$ | −0.12 |
| Haemophilus influenza | $1 \times 10^7$ | −0.34 |
| Escherichia coli | $1 \times 10^7$ | −0.44 |
| Enterobacter aerogenes | $1 \times 10^7$ | −0.23 |
| Mycobacterium leprae | $1 \times 10^7$ | −0.18 |

[1]denotes pfu in infected cells
[2]denotes proviral copies

Modifications of the above-described modes for carrying out the invention that are obvious to those of skill in biochemistry, nucleic acid hybridization assays, and related fields are intended to be within the scope of the following claims.

---

We claim:

1. A set of synthetic oligonucleotides useful as amplifier probes in a sandwich hybridization assay for HBV, comprising at least two different oligonucleotide probes, wherein each oligonucleotide probe consists of:

a first segment having a minimum length of 25 nucleotides and a maximum length of 100 nucleotides which segment is at least 90% complementary to a segment of HBV nucleic acid, wherein said first segment comprises a nucleotide sequence selected from the group consisting of SEQ ID NOS: 6–44; and a second segment consisting of a nucleotide sequence which is at least 90% complementary to an oligonucleotide segment of a nucleic acid multimer wherein said second segment and said multimer are not complementary to HBV nucleic acid;

and optionally one or more noncomplementary segments each consisting of a nucleotide sequence that is not complementary to HBV nucleic acid.

2. The set of synthetic oligonucleotides of claim 1, wherein each said second segment comprises SEQ ID NO:54.

3. The set of synthetic oligonucleotides of claim 1, wherein said set comprises from 5 to 100 different oligonucleotide probes.

4. The set of synthetic oligonucleotides of claim 1, wherein each of said first segments consists of a nucleotide sequence selected from the group consisting of SEQ ID NOS: 6–44.

5. A set of synthetic oligonucleotides useful as capture probes in a sandwich hybridization assay for HBV, comprising at least two different oligonucleotide probes, wherein each oligonucleotide probe consists of:

a first segment having a minimum length of 25 nucleotides and a maximum length of 100 nucleotides which segment is at least 90% complementary to a segment of HBV nucleic acid, wherein said first segment comprises a nucleotide sequence selected from the group consisting of SEQ ID NOS: 45–53; and a second segment consisting of a nucleotide sequence which is at least 90% complementary to an oligonucleotide bound to a solid phase wherein said second segment and said olignucleotide bound to a solid phase are not complementary to HBV nucleic acid;

and optionally one or more noncomplementary segments each consisting of a nucleotide sequence that is not complementary to HBV nucleic acid.

6. The set of synthetic oligonucleotides of claim 5, wherein each said second segment comprises SEQ ID NO:55.

7. The set of synthetic oligonucleotides of claim 5, wherein said set comprises from 5 to 100 different oligonucleotide probes.

8. The set of synthetic oligonucleotides of claim 5, wherein each of said first segments consists of a nucleotide sequence selected from the group consisting of SEQ ID NOS: 45–53.

9. A solution sandwich hybridization assay for detecting the presence of HBV nucleic acid in a sample, comprising (a) contacting the sample with (i) amplifier probes comprising the set of synthetic oligonucleotides of claim 1 and (ii) a set of capture probe oligonucleotides wherein there is a molar excess of amplifier probes and of capture probes over analyte nucleic acid in the sample, wherein said set of capture probe oligonucleotides comprises at least two different oligonucleotides each of which consists of a first segment having a minimum length of 25 nucleotides and a maximum length of 100 nucleotides which segment is at least 90% complementary to a segment of HBV nucleic acid, wherein said first segment comprises a nucleotide sequence selected from the group consisting of SEQ ID NOS: 45–53; and a second segment consisting of a nucleotide sequence which is at least 90% complementary to an oligonucleotide bound to a solid phase wherein said second segment is not complementary to HBV nucleic acid;

and optionally one or more noncomplementary segments each consisting of a nucleotide sequence that is not complementary to HBV nucleic acid;

(b) contacting the product of step (a) with said oligonucleotide bound to the solid phase;

(c) thereafter separating bound materials from those not bound to the solid phase;

(d) contacting the bound product of step (c) with a nucleic acid multimer, said multimer comprising at least one oligonucleotide segment that is at least 90% complementary to the second segment of the amplifier probe polynucleotide and a multiplicity of second oligonucleotide segments that are at least 90% complementary to a labeled oligonucleotide;

(e) removing unbound multimer from the solid phase complex of step (d);

(f) contacting the solid phase complex product of step (e) with the labeled oligonucleotide;

(g) removing unbound labeled oligonucleotide from the solid phase complex of step (f); and (h) detecting the presence of label in the solid phase complex product of step (g) and, thereby, detecting the presence of HBV nucleic acid in the sample.

10. The assay of claim 9, wherein said set of amplifier probes comprises from 5 to 100 different oligonucleotide probes.

11. The assay of claim 9, wherein said set of capture probes comprises from 5 to 100 different oligonucleotide probes.

12. A kit for the detection of HBV in a sample comprising in combination (i) a set of amplifier probe oligonucleotides comprising the set of oligonucleotides of claim 1;

(ii) a set of capture probe oligonucleotides comprising at least two different oligonucleotides each of which consists of a first segment having a minimum length of 25 nucleotides and a maximum length of 100 nucleotides which segment is at least 90% complementary to a segment of HBV nucleic acid, wherein said first segment comprises a nucleotide sequence selected from the group consisting of SEQ ID NOS: 45–53; and a second segment consisting of a nucleotide sequence which is at least 90% complementary to an oligonucleotide bound to a solid phase wherein said second segment is not complementary to HBV nucleic acid;

and optionally one or more noncomplementary segments each consisting of a nucleotide sequence that is not complementary to HBV nucleic acid;

(iii) a nucleic acid multimer, said multimer comprising at least one oligonucleotide segment that is at least 90% complementary to the second segment of the amplifier probe polynucleotide and a multiplicity of second oligonucleotide segments that are at least 90% complementary to a labeled oligonucleotide; and (iv) a labeled oligonucleotide which is at least 90% complementary to the second segment of the nucleic acid multimer of (iii).

13. The kit of claim 12, wherein said set of amplifier probes comprises from 5 to 100 different oligonucleotide probes.

14. The kit of claim 12, wherein said set of capture probes comprises from 5 to 100 different oligonucleotide probes.

* * * * *